United States Patent [19]
Brayton

[11] Patent Number: 5,756,049
[45] Date of Patent: May 26, 1998

[54] WATER TESTING CAPSULE USING WATER SOLUBLE FILM MEMBRANES

[75] Inventor: Scott V. Brayton, Ames, Iowa

[73] Assignee: Hach Company, Ames, Iowa

[21] Appl. No.: 740,225

[22] Filed: Oct. 25, 1996

[51] Int. Cl.[6] .................................................. G01N 33/18
[52] U.S. Cl. ......................... 422/61; 422/102; 436/39
[58] Field of Search .......................... 422/55–58, 61, 422/102; 436/163, 101, 103, 84, 110, 113, 39

[56] References Cited

U.S. PATENT DOCUMENTS

| | | |
|---|---|---|
| 3,721,528 | 3/1973 | Mead et al. |
| 3,992,158 | 11/1976 | Przybylowicz et al. ................ 422/56 |
| 4,099,939 | 7/1978 | Vancheri et al. ................ 55/246 |
| 4,522,923 | 6/1985 | Deutsch et al. ................ 436/536 |
| 4,857,453 | 8/1989 | Ullman et al. ................ 435/7 |
| 4,923,680 | 5/1990 | Nelson ................ 422/57 |
| 4,965,047 | 10/1990 | Hammond ................ 422/58 |
| 5,000,919 | 3/1991 | Heckmann ................ 422/58 |
| 5,137,690 | 8/1992 | Gernez ................ 422/57 |
| 5,182,216 | 1/1993 | Clayton et al. ................ 436/518 |
| 5,320,807 | 6/1994 | Brinton et al. ................ 422/61 |
| 5,356,814 | 10/1994 | Carrico, Jr. et al. ................ 435/286 |
| 5,384,096 | 1/1995 | Burns ................ 422/102 |
| 5,490,971 | 2/1996 | Gifford et al. ................ 422/58 |
| 5,500,375 | 3/1996 | Lee-Own et al. ................ 436/514 |
| 5,525,299 | 6/1996 | Lowe ................ 422/99 |

*Primary Examiner*—Lyle A. Alexander
*Attorney, Agent, or Firm*—Zarley, McKee, Thomte, Voorhees, & Sease

[57] ABSTRACT

A capsule package and a touch-free method for water analysis. It allows for addition of dry ingredients and aqueous test reagent without any human intervention, and therefore substantially decreases the possibility for analysis error. Furthermore, it eliminates physical contact between the operator and the chemical reagent, thereby enhancing safety. Importantly, the packaging system allows for film protection of a water soluble membrane so that it is damage free prior to use.

11 Claims, 4 Drawing Sheets

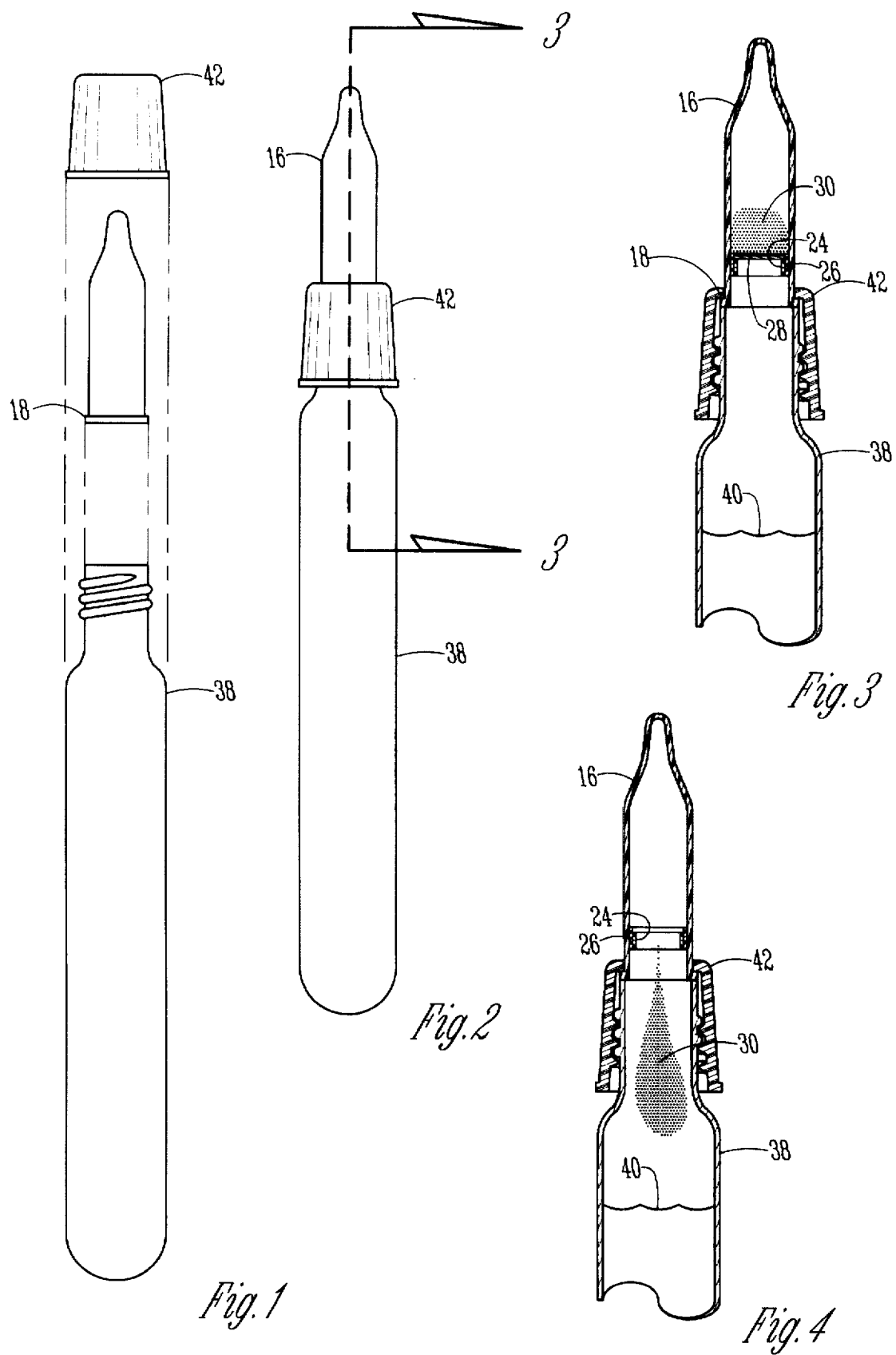

5,756,049

WATER TESTING CAPSULE USING WATER SOLUBLE FILM MEMBRANES

FIELD OF THE INVENTION

This invention relates to packaging systems and methods for testing water.

BACKGROUND OF THE INVENTION

It is recognized in the water treatment industry that water analysis to determine the degree of water purity must often be conducted by personnel that are not of high chemical skill. As a result, the test methods must be as foolproof as possible. The testing of municipal water, waste water, industrial waters and environmental waters frequently involve tests, such as chlorine testing, iron testing, phosphate testing, pH testing, ammonium testing, nitrate testing and testing for certain indicator bacteria. These tests, to be reliably run, involve use of quantified amounts of test reagent added to carefully controlled amounts of aqueous test sample. In this way, predictable physical and/or chemical changes, such as color changes, etc., can be measured that will then allow determination of the presence and amount of the target analyte. Typically, in such reactions dry test reagent is added in the form of "pillows" of solid reagent which are opened and then the contents dumped into a reagent test tube containing the aqueous water sample. The problem with use of reagent "pillows" is that while the "pillow" itself contains the precise amount needed, to accurately test a defined amount of aqueous solution, the reagent, after opening the "pillow", can come in contact with the operator's hands, can be spilled, or can have adulterating contaminants accidentally added. This creates significant chances for error. If error in the amount or condition of reagent added occurs, the test result, i.e. the conclusion reached based upon the test reaction itself, is subject to error. These errors can result in unnecessary, and at times even dangerous changes in water processing conditions predicated upon false readings.

The potential for reagent contact with the operator, either through spills onto the hands or through inhalation of dust, is a significant safety hazard. While it is good chemical hygiene to avoid contact altogether, in practice it is nearly impossible to eliminate some contact when transferring reagents. This inadvertent contact can severely affect operators who may exhibit allergic reaction to the specific chemical.

In the past, it has been known that dry test reagents and aqueous test sample can be separated, one from another, by a water soluble test membrane. See, for example, Deutsch et al., U.S. Pat. No. 4,522,923, issued Jun. 11, 1985, that relates to a sample of biological fluid and water with the aqueous sample flowing to each successive chamber, with the chambers separated by water soluble polymer layers that are dissolved. This patent and the test system are designed for home pregnancy testing. Such a contained membrane separated system never before has been applied to water testing, and never before has been designed to provide a packaging system that allows for protection of the water soluble film prior to use in an aqueous test system, such that it minimizes the risk of damage to the water soluble membrane prior to test use.

There is, therefore, a continuing need to develop a touch-free water test system. By touch-free, it is meant that the testing reagents and the aqueous sample are all contained in a closed system, and the test operator need merely intermix those. This full containment of all reagents inside of a closed system as is self evident, would result in less error risk and false readings in addition to eliminating the chemical contact hazard to the operator. This invention has, as its primary objective, the fulfillment of the above need for a touch-free system in the context of water testing.

Another objective of the present invention is to provide a water treatment packaging system that is touch-free and, which at the same time, provides package protection of a water soluble separating membrane such that its risk of damage prior to test use is minimized.

A yet further objective of the invention is to provide a method of testing of water which is human touch-free with respect to all reagents in the system in order to minimize false readings or errors in test results.

A further objective of the invention is to provide a human touch-free method to eliminate chemical reagent contact hazard, thus enhancing the safety aspect of the test system.

The method of accomplishing these and other objectives of the invention will become apparent from the following description of the invention.

BRIEF DESCRIPTION OF THE DRAWINGS

FIG. 1 is an exploded view of an aqueous sample test tube showing how the container capsules of the invention may be used in actual operation.

FIG. 2 shows the test reagent system of FIG. 1 in operational assembly.

FIG. 3 is a sectional view along line 3—3 of FIG. 2.

FIG. 4 shows the system of FIG. 3 with the water soluble membrane dissolved and a dry test reagent dropping into the aqueous test sample.

SUMMARY OF THE INVENTION

A capsule package and a touch-free method for water analysis. It allows for addition of reagents and aqueous test sample without any human intervention, and therefore substantially decreases the possibility for analysis error and chemical contact hazard. Importantly, the packaging system allows for film protection of a water soluble membrane so that it is damage free prior to use.

DETAILED DESCRIPTION OF THE INVENTION

Figure 5:
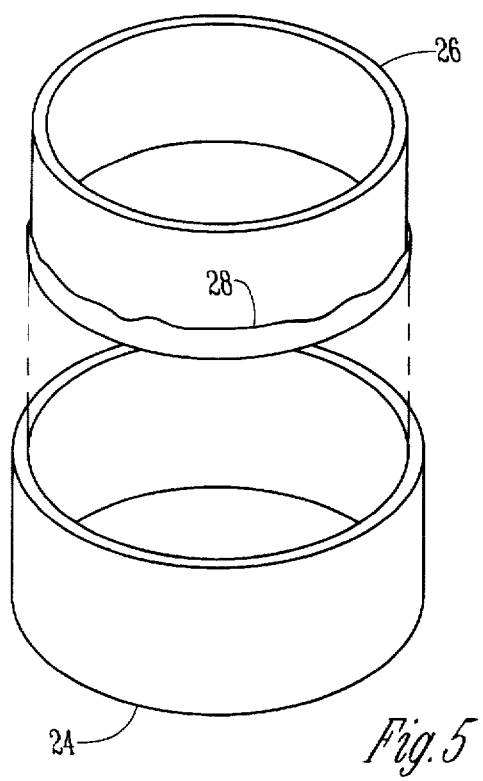
FIG. 5 shows the inner and outer capsule rings and captured water soluble membrane of the capsule container.
Figure 6:
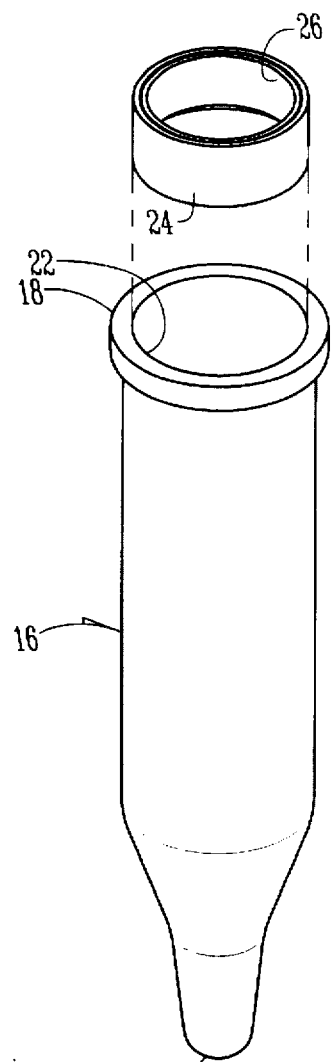
FIG. 6 shows the capsule container and the inner and outer capsule rings with captured membrane in exploded view.
Figure 7:
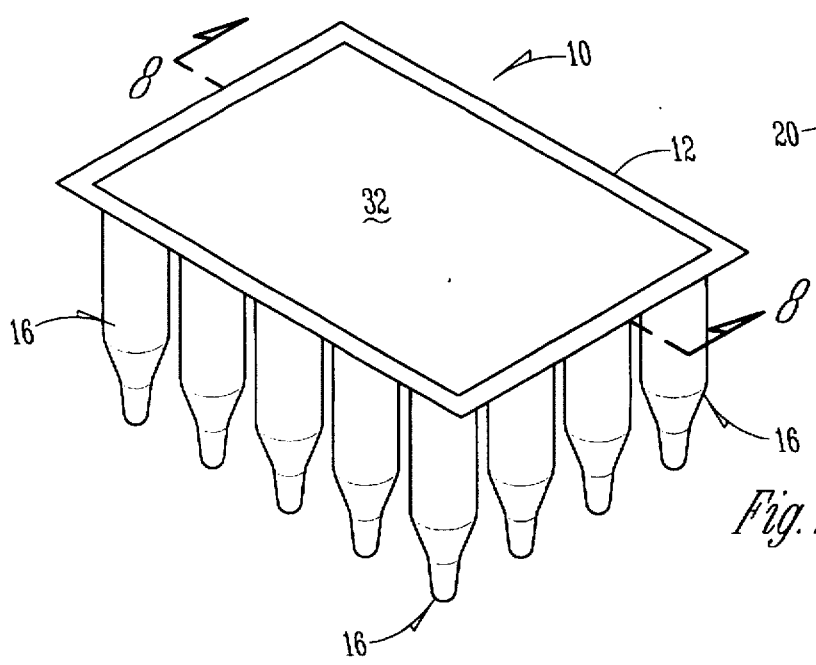
FIG. 7 shows the capsule package perspective view as used for containment of a plurality of touch-free water analysis capsules.
Figure 8:
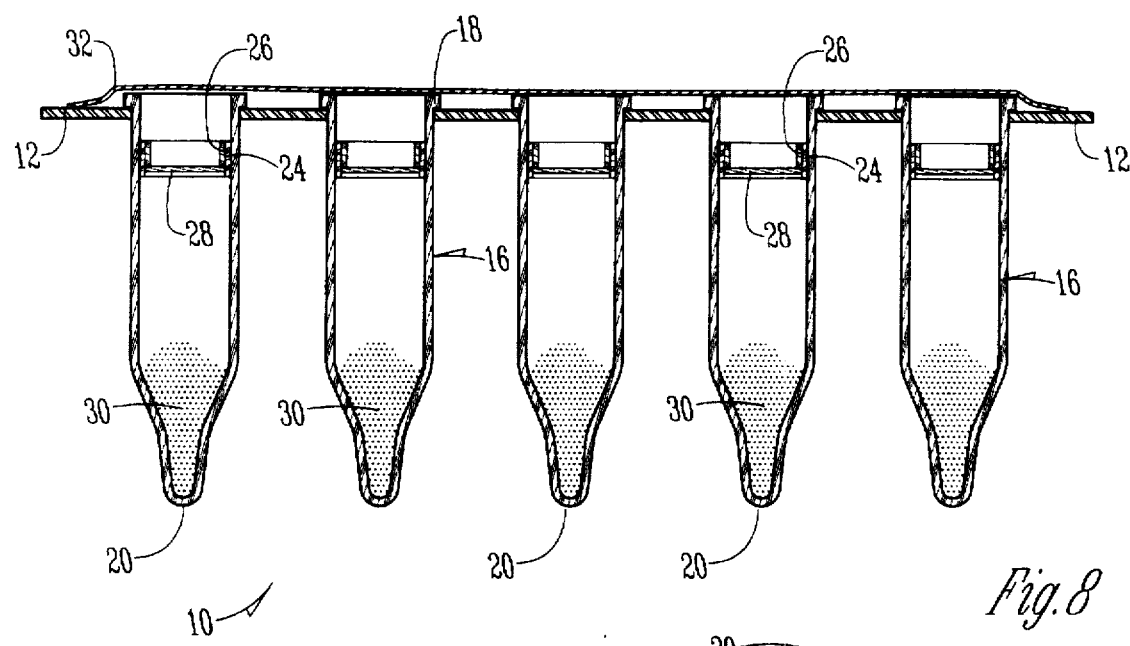
FIG. 8 shows a sectional view of the capsule package of FIG. 7 along line 8—8.

Packaging system 10 (FIG. 7) of the present invention is best shown in the perspective view of FIG. 7. In FIG. 7 there is shown capsule package 10 for touch-free water analysis. The capsule package 10 is comprised of a sheet of capsule holding material 12, typically a cardboard sheet with a series of arranged puncture holes (not depicted) of a circumference such that capsule containers 16 will fit through the puncture holes, but the cardboard sheet 12 will be caught by the capsule lip 18. Capsule container 16 (FIG. 6) has capsule lip 18, sealed capsule end 20, and capsule open mouth end 22. Capsules 16 are positioned through the open apertures (not depicted) and allowed to downwardly project, as illustrated in FIG. 7. Capsules 16 have an outer capsule ring 24 and an inner capsule ring 26 inserted concentrically into outer capsule ring 24. Positioned over the bottom of inner capsule ring 26 is a water soluble membrane 28. The use of an outer capsule ring 24 and an inner capsule ring 26 in nesting or concentric relationship is preferred because of ease of assembly. Water soluble membrane 28 can be made of a variety of water soluble materials, the most typical of which is polyvinyl alcohol. Others that may be used include water soluble cellulose derivatives, such as carboxymethyl cellulose, carboxyethyl cellulose, etc., or polyethylene oxide. However, polyvinyl alcohol is the preferred material because of its decent structural strength and its unquestioned high water solubility, as well as its easy availability. Polyvinyl alcohol and methyl hydroxy propyl cellulose, both of which can be used, are available, for example, from Chris Craft Industrial Products of South Holland, Ill. Inner rings 26 carrying polyvinyl alcohol membrane 28 and outer capsule ring 24 are inserted together as illustrated in FIG. 5 and inserted into the capsule open mouth end 22 as illustrated in FIG. 6. Capsule 16 contains a water soluble dry test reagent 30. Test reagent 30 can be any of a variety of water test reagents or powders. For example, if the test is designed for chlorine testing, the reagent may contain N,N-diethyl-p-phenylenediamine (DPD). If the test reagent is for iron testing, the reagent may contain 1,10-phenanthroline. If the test reagent is for phosphate testing, it can be a molybdenum compound and a reducing agent. If the test is for pH, it can be bromthymol blue or any other pH indicator. If the test is for ammonia, it can be based on the salicylate method. If the test is for nitrate, it can be based on a metallic nitrate-reducing agent such as a zinc combined with a diazonium coupling reaction. The test reagent 30 normally sits at the bottom of sealed end 20 as depicted in FIG. 8, and can be water soluble or water insoluble and while normally dry may be a liquid or gel reagent. Over the capsule open mouth 22 is positioned in laminar relationship a top foil barrier sheet 32, held into position by an adhesive. Natural or synthetic polymeric adhesives are readily available from companies such as 3M, and these are suitable for the use of adhering or securing top foil 32 to cardboard sheet 12. In this way, the capsule open mouth end 22 is sealed. Top foil sheet 32 is both moisture and gas impermeable. Thus, there is an effectively sealed relationship impervious to moisture or gases, and it is touch-free with respect to the process operator such that the interior of capsule 16 and the dry water soluble test reagent itself 30 are not touched. If the packaging system 10 is inverted from the position shown in FIG. 7, the dry powder reagent 30 simply falls against the polyvinyl alcohol membrane 28 as illustrated in FIG. 9.

Figures 9, 10:
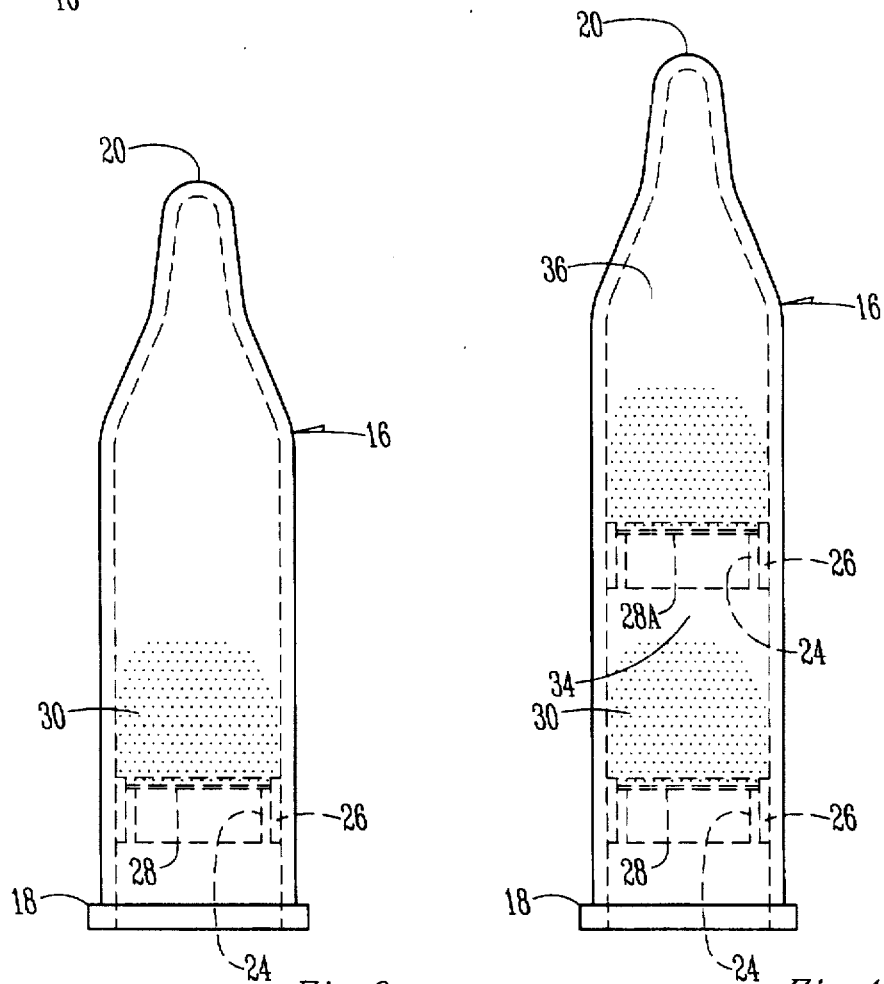
FIG. 9 shows an inverted capsule with the water soluble dry reagent pressing against the water soluble membrane.
FIG. 10 shows a capsule that uses two polyvinyl alcohol water soluble membranes to separate the capsule into two package compartments containing two dry reagents.

FIG. 10 illustrates a capsule 16 which has two polyvinyl alcohol membranes 28 and 28A. In this way, the capsule may be separated into two compartments as illustrated in FIG. 10, namely, compartments 34 and 36. The two capsule cartridge of FIG. 10 can be used in the system of FIG. 1 or FIG. 11.

Outer capsule ring 24 and inner capsule ring 26 may be made of a variety of materials, including relatively inert alphaolefin polymeric plastics such as polypropylene and polyethylene. Such are readily available.

In use, the individual capsules 16 of the packaging system 10 of FIG. 7 may be used in the following manner. One capsule 16 is grabbed by the test operator and pulled downwardly from its position shown in FIG. 7. Since the cardboard sheet 12 is somewhat flexible, pulling away from it will release capsule 16. Capsule 16 can then be inverted to the position shown in FIG. 9 such that the water soluble dry test reagent 30 falls against polyvinyl alcohol membrane 28. A tube 38 (see FIG. 1) containing aqueous test solution 40 is provided. Capsule 16 is inserted through the upper aperture of screw cap 42 and threadably screwed onto aqueous sample test tube 38 in the manner depicted in FIG. 2. Thereafter, the aqueous sample tube 38 is inverted such that the aqueous sample 40 contacts polyvinyl alcohol membrane 28. After a short period of contact, membrane 28 dissolves, and dry, water soluble test reagent 30 falls into the aqueous test solution 40, as depicted in FIG. 4, with the resulting reaction occurring. Typically, calorimetric detection of change is then measured to determine the presence or absence and/or the quantitative concentration of the material tested, for example, chlorine or iron or phosphate or pH or ammonium or nitrate ions. In this way, the amount of dry test reagent 30 is absolutely controlled, there is no risk of spillage or contamination, and the test is therefore essentially error-free. Operator touch-free aspect eliminates chemical contact hazard, thereby enhancing safety. Moreover, because of the design of the packaging system, risk of damage to the fragile membrane 28 is minimized.

Figure 11:
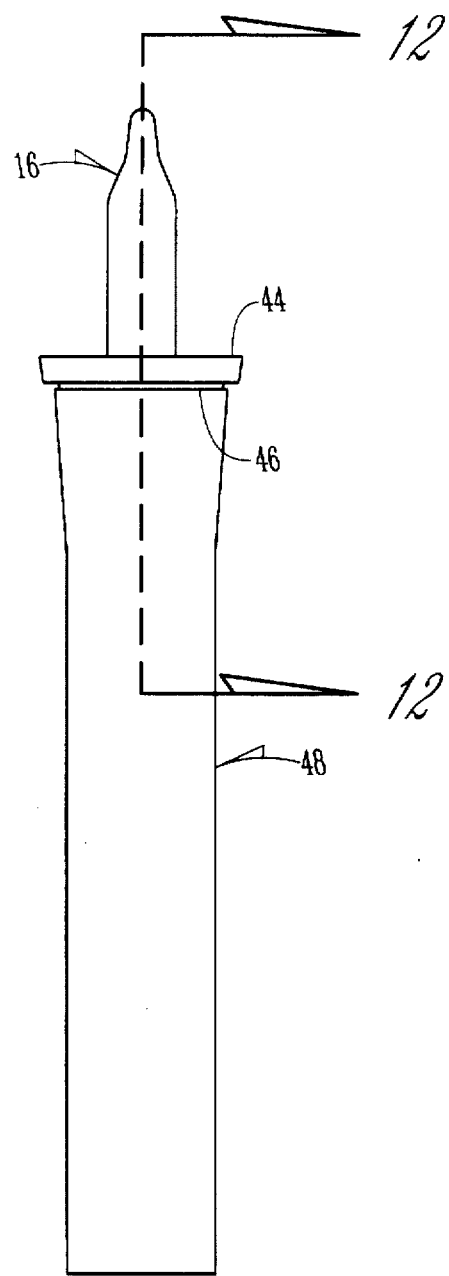
FIG. 11 shows an operational view of an alternative system of FIG. 1 and FIG. 2, with the capsule using a capsule plug collar as opposed to a capsule screw cap.
Figure 12:
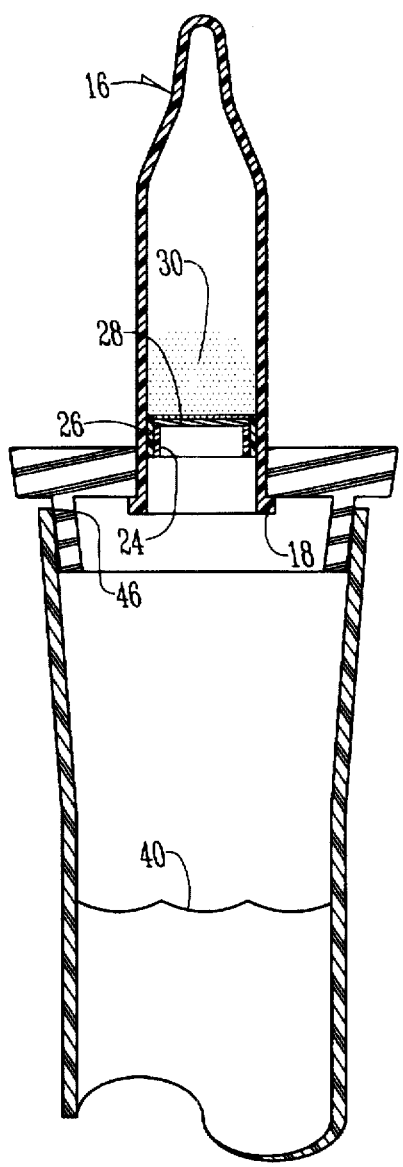
FIG. 12 shows the system of FIG. 11 with the water soluble dry test reagent against the membrane ready for use in the touch-free system.

FIGS. 11 and 12 show an alternative system to that demonstrated in FIGS. 1 and 2. In this system, the capsule 16 is not used with a threaded screw cap 42, but instead is inserted through an aperture in capsule plug collar 44. Capsule plug collar 44 is of such construction that it fits within the open mouth 46 of aqueous sample test tube 48. Either system works equally as well.

It can be seen from the above that the invention accomplishes at least all of its stated objectives. It is an effective water testing system. It uses a touchless approach, avoiding the use of dry ingredient "pillows" which may cause error. Furthermore, it eliminates physical contact with the chemical reagent, thereby providing enhanced operator safety. It uses a film to separate aqueous test sample from water soluble dry test reagent, and the film is protected from damage because of the packaging system. Moreover, the system is convenient, inexpensive, and easy to manufacture.

It goes without saying that certain constructional features of the invention may be changed without departing from the spirit and scope of the invention, and these changes, together with the equivalence of those specifically shown, are intended to be encompassed within the scope and spirit of the claimed invention.

What is claimed is:

1. A capsule package for touch-free water analysis, comprising:

a sheet of capsule holding material having at least one aperture formed in said sheet;

at least one capsule container extending through said aperture of said holding material;

said capsule container having one sealed end and one open mouth end;

a moisture and gas impermeable barrier sheet covering at least a portion of said holding material and the mouth end of said capsule container to seal the mouth end of said capsule container;

said capsule containing a water test reagent and having a water soluble barrier membrane across said open mouth end of said capsule; and whereby said capsule container may be pulled free of said capsule package and used in a reagent touch-free water analysis.

2. The capsule package of claim 1 wherein the water soluble barrier membrane is polyvinyl alcohol.

3. The capsule package of claim 1 wherein the sheet of capsule holding material is cardboard.

4. The capsule package of claim 1 wherein the moisture and gas impermeable barrier is a foil covering sheet.

5. The capsule package of claim 1 wherein the capsule has at least two water soluble membranes to separate the capsule into more than one compartment.

6. The capsule package of claim 1 wherein the test reagent is selected from the group consisting of test reagents for water analysis. Examples include chlorine testing, iron testing, phosphate testing, pH testing, ammonia testing and nitrate testing.

7. The apparatus of claim 1 wherein said barrier sheet is secured to said holding material such that when the capsule container is pulled free from the capsule package, the mouth end of the capsule container becomes unsealed.

8. The apparatus of claim 7 wherein said barrier sheet is secured to said holding material by an adhesive.

9. The apparatus of claim 1, further comprising a lip formed on the capsule container proximate the open mouth end, wherein said lip has a diameter larger than a diameter of the aperture formed in the sheet of holding material.

10. A capsule package for touch-free water analysis comprising:

a sheet of capsule holding material;

a plurality of apertures formed in said capsule holding material;

a plurality of capsule containers, each extending at least partially through one of said apertures in said capsule holding material;

at least one barrier sheet secured to the capsule holding material and disposed over at least one of said apertures of said capsule holding material and covering a portion of at least one of said capsule containers;

each of said capsule containers containing a water test reagent and having a water soluble barrier membrane containing said water test reagent within said capsule container; and wherein each of said capsule containers can be pulled from the sheet of capsule holding material and from the barrier sheet and used in a reagent touch-free water analysis.

11. The apparatus of claim 10, wherein each of said capsule containers includes an open end, wherein the barrier sheet seals the open end of the capsule containers while the capsule containers are extended through the apertures in the capsule holding material.

* * * * *